United States Patent [19]
Haber

[11] Patent Number: 4,552,128
[45] Date of Patent: Nov. 12, 1985

[54] ELASTOMECHANICAL SPHINCTER

[76] Inventor: Terry M. Haber, 25011 Castlewood, Lake Forest, Calif. 92630

[21] Appl. No.: 566,486

[22] Filed: Dec. 29, 1983

[51] Int. Cl.[4] ............................................. A61B 19/00
[52] U.S. Cl. ............................ 128/1 R; 128/DIG. 25; 128/346; 251/7
[58] Field of Search ............... 128/346, DIG. 25, 1 R; 251/4, 5, 7, 75

[56] References Cited
U.S. PATENT DOCUMENTS 3,903,894  9/1975  Rosen et al. ............................ 251/5
3,926,175 12/1975  Allen et al. ......................... 128/D25
4,340,061  7/1982  Kees, Jr. et al. ..................... 128/346

Primary Examiner—S. C. Pellegrino
Assistant Examiner—Karen L. Kaechele
Attorney, Agent, or Firm—Morland C. Fischer

[57] ABSTRACT

An elastomechanical sphincter comprising a prosthetic device for implantation about a patient's lumen such as the urethra for closing and opening the lumen. The prosthetic sphincter includes a body of flexible polymeric material configured to define an articulating structure having an elongated occlusion orifice arranged to embrace the patient's urethra with minimal ischemic interruption of circulatory blood flow. An integrally formed manually manipulable pressure relief cuff extends from a peripheral portion of the articulating structure in such a manner that physical pulling on the pressure relief cuff in a direction transverse to the elongation of the occlusion orifice will open the orifice which thereby opens the lumen. The natural elasticity of the device results in a closing of the lumen upon releasing of the pressure relief cuff. In one embodiment, by way of example, the pressure relief cuff may be positioned within the folds of the loose skin of the posterior scrotum. The elastomechanical sphincter is configured such that some patients will be able to operate the device automatically, using only internal force generated by natural contraction of muscle tissue within their bodies.

25 Claims, 10 Drawing Figures

ELASTOMECHANICAL SPHINCTER

BACKGROUND OF THE INVENTION

1. Field of the Invention

This invention relates generally to prosthetic devices and more particularly, to an elastomechanical sphincter for implantation in a patient to overcome the problem of incontinence.

2. Background of the Invention

In my U.S. Pat. No. 4,401,107 there is described an Intestinal Control Valve which can be surgically implanted without invading the intestine itself. While the valve disclosed is primarily designed to achieve continence within the distal intestine of a patient, it could also be used in a smaller version to close off the urethra.

In my later filed copending patent application Ser. No. 435,761 entitled Prosthetic Sphincter, there is disclosed an improved closure device in the form of an artificial sphincter wherein there is no need for any type of electrical drive motor. Rather, a flexible force-applying means is utilized to actuate the device from a remote location.

In my more recent copending patent application Ser. No. 552,107 entitled Mechanical Prosthetic Sphincter, there is shown a further closure device which can occlude and articulate the distal intestine, the urethra, or other such lumen, where no electrical power at all is necessary but rather the device is wholly mechanically operated. In this respect, a flexible force-applying means is used so that the actuating component can be located at an accessible position relative to the sphincter occlusion element itself.

Along the line of the aforementioned constructions, it is also desirable to provide an improvement in the construction of a prosthetic sphincter capable of articulating and occluding a lumen, such as the urethra, utilizing a decreased number of components than has been thought necessary heretofore.

SUMMARY OF THE INVENTION

With the foregoing in mind, the present invention contemplates a vastly improved prosthetic sphincter, herein termed an elastomechanical sphincter, particularly useful in closing off the urethra wherein pneumatic or hydraulic mediums, tubing which kinks and leaks, mechanical connecting cables, electrically-driven motors and the like, as have characterized prior devices, are wholly eliminated. Also the mechanical strangulation of blood flow within the lumen, resulting in ischemic tissue erosion, is vastly minimized or eliminated by virtue of the inherent flexibility of the elastomechanical sphincter.

More particularly, the present sphincter comprises a body of resilient polymer material configured to define an articulating structure having a normally closed elongated occlusion orifice for surrounding a lumen such as the urethra. An integrally formed manually manipulable, pressure relief cuff extends from a peripheral portion of the articulating structure.

Appropriate suture attachment means are provided to secure spaced peripheral areas of the articulating structure to adjacent bone or tissue structure in a patient such that the articulating structure can surround and gently embrace the urethra with the pressure relief cuff protruding against a loose skin area of the patient. The arrangement is such that the patient can manually grasp the pressure relief cuff by compressing the skin on either side of the cuff and then pulling the cuff away from the articulating structure in a direction transverse to the elongated occlusion orifice so that said occlusion orifice opens and, in turn, permits the urethra to open. Releasing of the pressure relief cuff to its natural orientation results in automatic closing of the occlusion orifice about the urethra.

BRIEF DESCRIPTION OF THE DRAWINGS

A better understanding of this invention will be had by now referring to the accompanying drawings in which.

DETAILED DESCRIPTION OF THE PREFERRED EMBODIMENT

Figure 1:
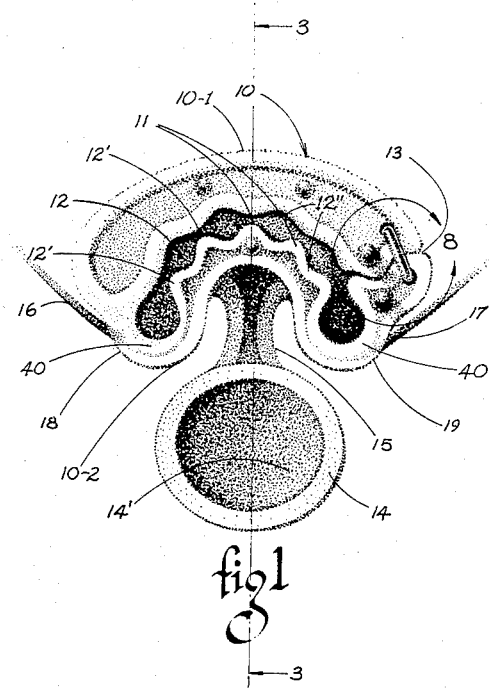
FIG. 1 is a front elevational view of the elastomechanical sphincter of this invention showing the same in its normal closed condition about a patient's urethra.
Figure 2:
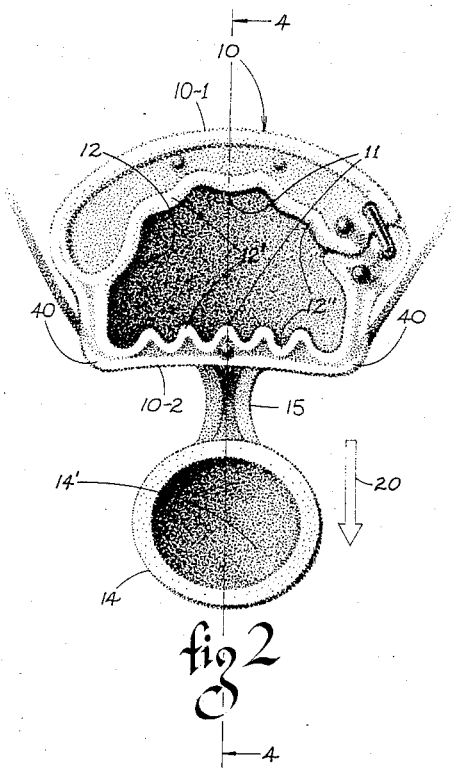
FIG. 2 is a view similar to FIG. 1 but illustrating the relative positions of parts of the device when in open condition to unblock the urethra.

Referring to FIGS. 1 through 4, the elastomechanical sphincter includes a body of resilient polymeric material, such as silicone or the like, having a spring-like memory and being shaped to define an articulating structure 10. As is best shown in FIGS. 1 and 2, the articulating structure 10 comprises upper and lower halves 10-1 and 10-2 hingedly connected together by oppositely disposed and coextensively formed hinges 40. Hinges 40 are arcuately shaped (rather than point hinges) so as to better distribute, and thereby minimize, forces associated with opening and closing the articulating structure, whereby to maximize the life expectancy of the disclosed sphincter and minimize compression setting thereof. The upper and lower articulating halves 10-1 and 10-2 are arranged (in the closed position of FIG. 1) in substantially parallel alignment and adapted for reciprocal movement relative to one another whereby to selectively control the flow of material therepast. Because of the reciprocal movement of articulating structure halves 10-1 and 10-2 in a single plane, the articulating structure 10 may be advantageously characterized as a minimal friction-inducing device, so as to minimize any possibility of tissue erosion due to ischemic necrosis. The articulating structure 10 has a normally closed elongated occlusion orifice 11 for surrounding a lumen 12. In the particular embodiment to be described, the lumen 12 constitutes a patient's urethra. However, it is also to be understood that the presently disclosed articulating structure 10 is also applicable to a lumen which is the intestine, the esophagus, a vein, an artery or the vas deferins.

A series of alternating pressure concentrating ridges 12' and pressure relief troughs 12" extend from articulating structure 10 around the periphery of the occlusion orifice 11. The pressure concentrating ridges 12' transmit occlusive forces from the articulating structure 10 to close the lumen 12. The pressure relief troughs 12" minimize the occlusion of axial blood vessels supplying the lumen 12 by providing paths of relatively lower barometric pressure extending longitudinally through articulating structure 10 so as to maximize freedom of arteriovascular blood flow and thereby minimize the chance of ischemic erosion to the delicate tissues.

In order to position the occlusion orifice about the patient's urethra, the articulating structure 10 includes a channel 13 extending from an exterior surface into the occlusion orifice 11. This channel 13 permits spreading of the articulating structure to enable the occlusion orifice to embrace the urethra. The manner in which the channel is secured together after implantation and positioning of the device about the urethra will be described subsequently.

Figure 3:
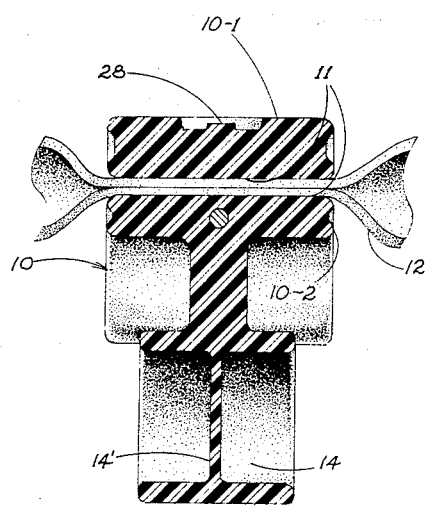
FIG. 3 is a cross section taken in the direction of the arrows 3—3 of FIG. 1.
Figure 4:
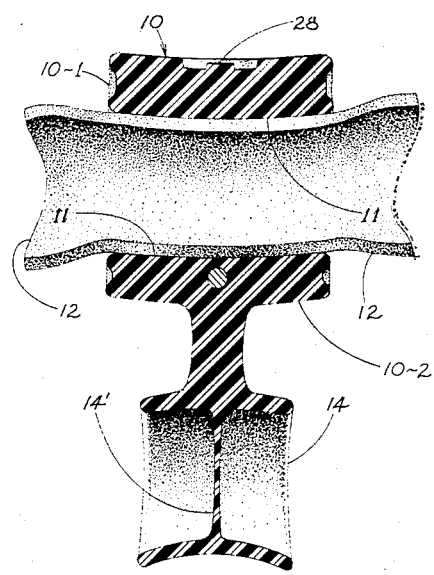
FIG. 4 is a cross section taken in the direction of the arrows 4—4 of FIG. 2.

Referring to the lower portion of FIG. 1, the articulating structure further includes a flexible and integrally formed manually manipulable pressure relief cuff 14 extending from a peripheral portion of the articulating structure as by integral extension portion 15. Pressure relief cuff 14, as shown, is preferably elliptically ring-shaped and may be provided with a supporting membrane 14', lying in the plane of the ring-shape midway between opposite sides of the ring as best shown in FIG. 3. Supporting membrane 14' allows a flexible compression of relief cuff 14 while providing transverse support therefor.

In order to secure the sphincter in place, there are provided suture attachment means 16 and 17 secured to spaced peripheral areas 18 and 19 of the articulating structure 10. Means 16 and 17 extend away from the articulating structure for suitable connection to adjacent bone or tissue structure in a patient, such as the ischium of the pelvis or the crura of the penis.

FIG. 2 illustrates the contorted position of the articulating structure 10 when the pressure relief cuff 14 has been pulled downwardly in the direction of the arrow 20; that is, in a direction transverse to the elongated occlusion orifice. As will be clear from both FIGS. 2 and 4, pulling downwardly on the cuff 14 serves to open the occlusion orifice and thus the urethra 12 so as to permit material to move therethrough. It will be understood that because of the spring-like memory of the sphincter, when the pressure relief cuff 14 is released, the articulating structure 10 will resume its normal configuration illustrated in FIGS. 1 and 3 so that the urethra is normally held occluded and continent.

From the foregoing, it will be evident that by providing the appropriate elastic or resilient polymeric material and by properly molding the same to provide the configuration described in the drawings, the opening and closing of the lumen or urethra can be effected by simply pulling on the pressure relief cuff and subsequently relaxing the pressure relief cuff. In some cases however, the patient will be able to automatically manipulate and control the sphincter by means of intraluminal pressure, such as that generated by biochemical or muscle forces naturally occurring from within the patient's body to permit the passage of urine, blood, or other intraluminal bodily materials.

Figure 5:
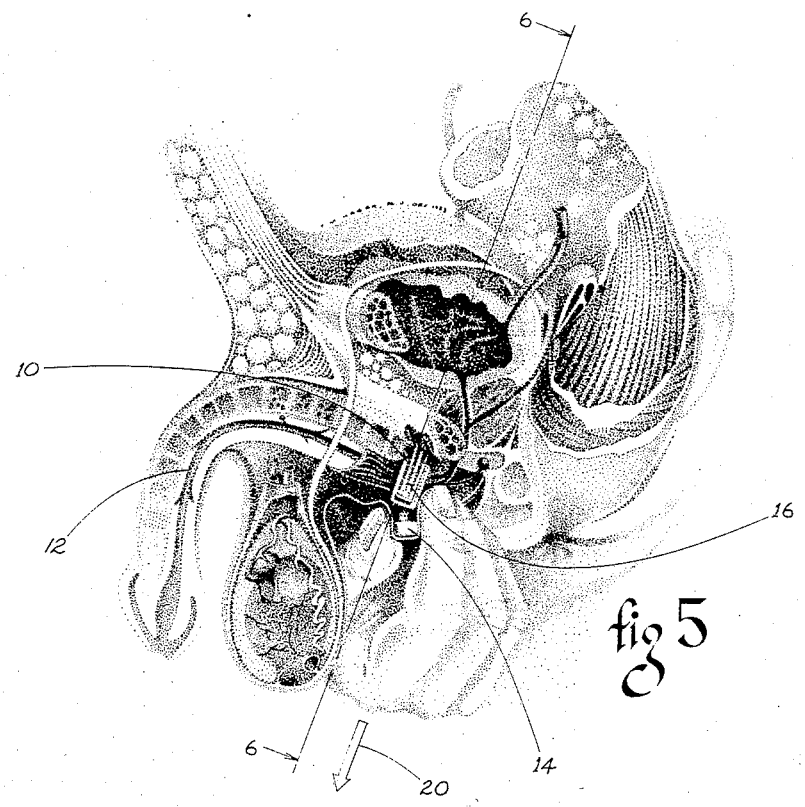
FIG. 5 is a broken away anatomical view of a patient's urethra with the elastomechanical sphincter of this invention in place illustrating how the same is operated.

Referring now to FIG. 5, there is shown a preferred location of the sphincter for closing of the urethra and opening the urethra. As shown in FIG. 5, the articulating structure surrounds the bulbous urethra with the pressure relief cuff 14 extending below as described with respect to FIGS. 1 through 4, the pressure cuff being adjacent to a loose skin area of the patient such as the skin adjacent and anterior to the anus and/or the superior-posterior aspect of the scrotum. In FIG. 5, there is shown diagrammatically a person's thumb and index finger pulling downwardly in the direction of the arrow 20 to open the occlusion orifice as described with respect to FIGS. 2 and 4.

Figure 6:
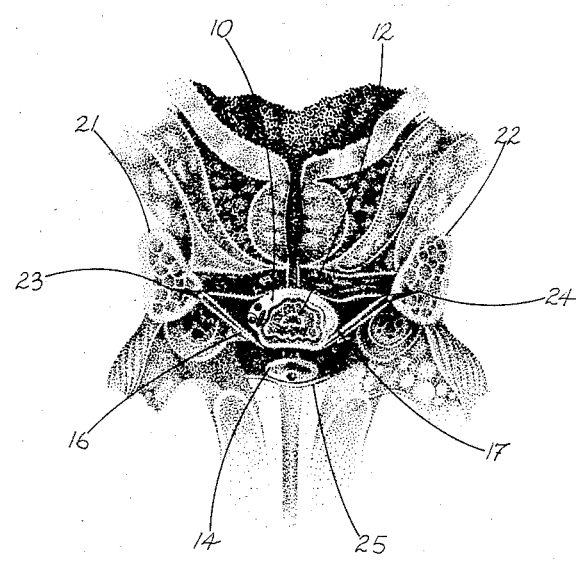
FIG. 6 is a cross section taken in the direction of the arrows 6—6 of FIG. 5.

FIG. 6 illustrates more clearly the manner in which the suture attachment means 16 and 17 are secured to the bone or tissue such as indicated at 21 and 22, this bone preferably constituting the ischium of the pelvis or the tissue constituting the crura of the penis. The actual supporting structure for the attachment thereof can be effected by appropriate orthopedic staples 23 and 24 respectively, as shown in FIG. 6. Also shown in FIG. 6 at 25 is the loose skin area bordering a part of the pressure relief cuff 14. As described heretofore, when the patient manually releases the pressure relief cuff which he has grasped by compressing the loose skin bordering either side of the cuff, the pressure relief cuff will return upwardly as the natural elasticity of the articulating structure closes the elongated occlusion orifice about the urethra.

Figure 7:
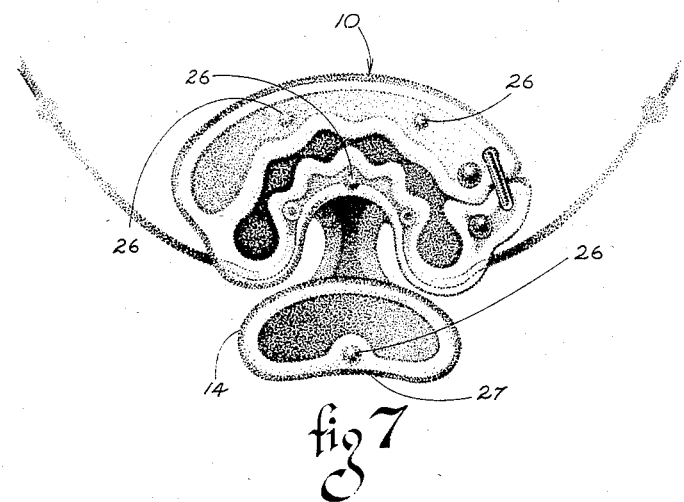
FIG. 7 is another front elevational view of the elastomechanical sphincter in its closed position showing a modified configuration.

Referring now to FIG. 7, there again is shown an elastomechanical sphincter similar to that described in FIGS. 1 through 4 but wherein there are included spherical telemetry elements 26 embedded in the articulating structure 10 about the elongated occlusion orifice so that all positions of the sphincter can be fluoroscopically monitored while in situ. In FIG. 7, the pressure relief cuff 14 is shown somewhat contorted at its bottom, the same being depressed upwardly as at 27. This is the shape that the pressure relief cuff 14 would assume when a person is sitting down, in view of the orientation in a fairly upright position of the sphincter device, as descibed in FIGS. 5 and 6. This deformation of the pressure relief cuff 14 into an ellipseoid-shape will result in a slight upward force on the articulating structure 10 serving further to occlude the urethra so that there is provided additonal continence safety factor for the patient while in a seated position, without including pain through a pressure relief cuff which does not deform and collapse for patient discomfort.

Figure 8:
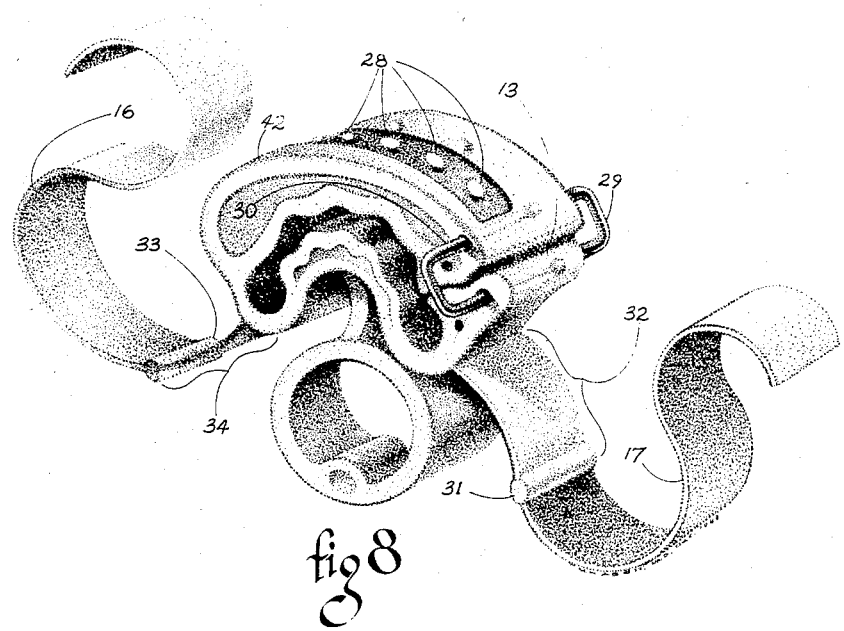
FIG. 8 is a perspective view of the sphincter of FIG. 7 useful in explaining attachment means used in securing the sphincter in place about a lumen.

In the perspective view of FIG. 8, the sphincter is similar to that described already except that a supporting membrane is not included in the ring-shaped pressure relief cuff. It will be noted that the top of the articulating structure has integral encoding areas 28 for appropriate serialization of the devices and subsequent identification and traceability thereof.

The embodiment of FIG. 8 also shows more clearly an appropriate attachment means for closing the channel 13 after the articulating structure has been positioned about the urethra or lumen. As shown, this attachment means takes the form of a pair of U-shaped closure staples 29 and 30 with extending legs terminating in conical-shaped, rounded protrusions of larger diameter than the legs. With this arrangement, the closure staples can be pressure-inserted into opposite sides of the articulating structure straddling the channel 13, the conical-shaped, rounded protrusions, temporarily spreading and stretching the flexible polymer material of the articulating structure and the lengths of the closure staple legs being greater than the thickness of said articulating structure so that the protrusions extend out the opposite sides of the articulating structure to hold the closure staples in place. It will be noted (as illustrated in FIG. 7) that two end protrusions for one of the closure staples are protruding. On the other hand, the U-shaped base of the other staple is shown extending in a parallel and opposite direction.

As is best shown in FIG. 8, a further feature of this invention involves the encapsulating with silicone, polyurethane, or the like, of the proximal extending ends of the suture attachment means 16 and 17 from the sphincter articulating structure. In this respect, there is provided an intermediate cylindrical terminating shape 31 in the suture attachment means 17 up to which encapsulation takes place as indicated at 32. A similarly terminating cylinder shape 33 is provided in the other suture attachment means 16 and the area between this cylinder and the exit point from the articulating structure is encapsulated in silicone, polyurethane, or the like, as indicated at 34. This encapsulation stabilizes the suture attachment means and assures complete vulcanization of said suture attachment means to the articulating structure during the molding of the elastomechanical sphincter itself. Said suture attachment means also provide flexible yet non-extensible reinforcement means to strengthen the hingedly manipulable portions of the articulating structure.

Figure 10:
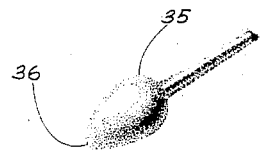
FIG. 10 shows a portion of the closure staple of FIG. 9 encircled within the circular arrow 10.
Figure 9:
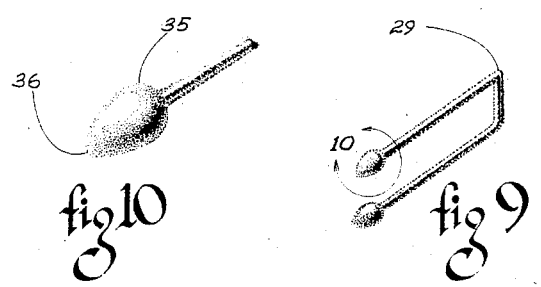
FIG. 9 is a perspective view of a closure staple utilized in the embodiment of FIG. 8.

FIG. 9 shows a perspective view of a typical fastening means in the form of the closure staple 29 described in FIG. 8 and FIG. 10 is an enlarged fragmentary view of the end of the leg constituting an enlarged portion 35 with a conical rounded shape 36. It will be noted that the diameter of the enlargement 35 is greater than the diameter of the leg so that once the same is forced out the exit opening on one side of the channel 13 in the articulating structure, it will essentially hold itself in place until an exponentially greater force in the opposite direction is applied to facilitate extraction and removal of the closure stable.

From all of the foregoing, it will now be evident that the present invention has provided a greatly improved sphincteric device wherein no pneumatic or hydraulic mediums, tubing prone to kinking and/or leaking, or electrical components are required, nor are any mechanical-type cables interconnecting to components required. The entire structure constitutes essentially a single integral molded part except for the suture attachment means which are molded in place as described so that they can be easily affixed to surrounding bone or tissue during implantation. The described closure staples 29 are easily inserted after the articulating structure and the corresponding elongated occlusion orifice has been positioned about the lumen or urethra.

Changes falling within the scope and spirit of this invention will occur to those skilled in the art. The elastomechanical sphincter is therefore not to be thought of as limited to the specific embodiments set forth herein for illustrative purposes. By way of example, it is also within the scope of the present invention to modify the surface texture (designated 42 in FIG. 8) of the disclosed sphincter to control tissue ingrowth thereon. More particularly, to inhibit fibrous tissue ingrowth, a polished or plated sphincter surface texture is provided. However, to encourage tissue ingrowth onto the sphincter, a porous surface is otherwise provided. Such tissue ingrowth may stabilize the position of the sphincter without the need for the suture attachment means (of FIGS. 7 and 8). Moreover, a temporary suture attachment means, such as polyglycolic acid mesh, may also be employed to temporarily position the sphincter until such adequate tissue ingrowth occurs as to achieve permanent sphincter stabilization.

I claim:

1. An elastomechanical sphincter comprising, in combination:
   (1) an articulating structure formed from a resilient material with a spring-like memory and having a normally closed elongated occlusion orifice for surrounding a lumen,
   (2) an elastic and manually manipulative pressure relief cuff extending outwardly from a peripheral portion of the articulating structure, said pressure relief cuff comprising a terminal end and an extensible neck portion extending between said terminal end and said articulating structure in a direction generally perpendicular to the direction of the lumen through said occlusion orifice, said pressure relief cuff being implanted at a location within the body of the patient such that said terminal end thereof is manually accessible to the patient so as to be pulled away from said articulating structure in said generally perpendicular direction to stretch said neck portion and thereby and contort the shape of said articulating structure, so that said occlusion orifice opens and in turn, permits the lumen to open, the relaxing of said neck portion resulting in the return of said orifice to the normally closed position to thereby close the lumen; and
   (3) suture attachment means secured to spaced peripheral areas of said articulating structure and extending for connection to adjacent bone or muscle tissue in a patient to secure the articulating structure within the patient in a position surrounding the lumen.

2. A sphincter according to claim 1, in which said elongated occlustion orifice for surrounding a lumen incorporates around the periphery of said orifice alternately positioned pressure concentrating means which transmit occlusive forces to said lumen and pressure reduction means which provide paths of lowered pressure to maintain maximum freedom of blood flow thereby minimizing damage to delicate tissues by ischemic strangulation.

3. A sphincter according to claim 2, in which said pressure concentrating means are alternately-positioned convex ridges, and said pressure reduction means are alternately-positioned concave throughs.

4. A sphincter according to claim 1, in which said pressure relief cuff terminal end is of a ring shape.

5. A sphincter according to claim 4, including an integral supporting membrane extending in the plane of said ring-shaped terminal end approximately midway between the opposite sides thereof.

6. A sphincter according to claim 1, in which said articulating structure includes a channel extending from an outer surface portion into said elongated occlusion orifice to permit spreading of the articulating structure so that said occlusion orifice can be positioned around the lumen; and detachable means for securing said channel in a closed condition after said occlusion orifice has been positioned to surround the lumen.

7. A sphincter according to claim 6, in which said detachable means includes at least one U-shaped closure staple with extended legs terminating in protrusions of larger diameter than the legs, whereby said closure staple can be inserted into said articulating structure temporarily stretching the resilient material thereof and straddling said channel, the length of the legs being greater than the thickness of said articulating structure so that the protrusions extend out of the articulating structure to hold the closure staple in place.

8. A sphincter according to claim 1, including telemetry elements associated with said articulating structure so that positions of the sphincter can be monitored by X-ray visualization while in situ.

9. A sphincter according to claim 1, wherein said articulating structure is fabricated from a resilient polymer material and the proximal portion of said suture attachment means extending from said articulating structure is encapsulated with said polymer material to stabilize the position of said suture attachment means and provide vulcanization of said suture attachment means to said articulating structure during formation of said sphincter.

10. A sphincter according to claim 1, in which said lumen is the urethra.

11. A sphincter according to claim 1, in which the lumen is the intestine.

12. A sphincter according to claim 1, in which the lumen is the esophagus.

13. A sphincter according to claim 1, in which the lumen is an artery.

14. A sphincter according to claim 1, in which the lumen is a vein.

15. A sphincter according to claim 1, in which the lumen is the vas deferins.

16. A sphincter according to claim 1 upon which a polished surface texture is provided to minimize fibrous tissue ingrowth onto said sphincter.

17. A sphincter according to claim 1 upon which a porous surface texture is provided to encourage tissue ingrowth for purposes of stabilizing the position of said sphincter.

18. A sphincter according to claim 1, wherein said articulating structure includes upper and lower hingedly interconnected sections surrounding the lumen, said upper and lower sections arranged in substantially parallel alignment and adapted for reciprocal movement relative to one another through a single plane so as to either open or close the occlusion orifice and the lumen being surrounded thereby.

19. An elastomechanical sphincter comprising a prosthetic device suitable for implantation so as to embrace a patient's lumen for closing and opening the lumen and selectively controlling the movement of material therethrough, said sphincter having a body formed from a resilient material having a spring-like memory, said body including an elastic normally closed occlusion orifice to surround and close the lumen to inhibit material movement therethrough, and an elastic pressure relief means extending outwardly from said sphincter body and comprising a terminal end and an extensible neck portion extending between said terminal end and said sphincter body in a direction generally transverse to the direction of the lumen through said occlusion orifice, said terminal end positioned against an accessible and palpable area of the patient's skin so as to be manually pulled by the patient in said generally transverse direction to stretch said neck portion and cause a contortion of said resilient sphincter body and thereby open said elastic occlusion orifice thereof and permit the movement of material through the lumen.

20. The elastomechanical sphincter according to claim 19, wherein said sphincter body comprises a pair of articulating sections hingedly connected together for surrounding the patient's lumen, said articulating sections arranged in substantially parallel alignment and adapted for reciprocal movement relative to one another so as to either close or open the occlusion orifice and thereby inhibit or permit the movement of material through the patient's lumen.

21. The elastomechanical sphincter according to claim 19, also including suture attachment means secured to said sphincter body and extending outwardly therefrom for connection to adjacent bone or muscle tissue of the patient in order to locate said sphincter at a position surrounding the lumen.

22. The elastomechanical sphincter according to claim 19, also including a series of alternating pressure relief troughs and pressure concentrating ridges formed around the occlusion orifice of said sphincter body, said pressure relief troughs providing paths through said orifice to minimize the occlusion of blood flow within the patient's lumen and said pressure concentrating ridges transmitting occlusive forces to occlude the lumen.

23. The elastomechanical sphincter according to claim 22, also including a channel extending through said sphincter body to said occlusion orifice, said sphincter body being spread at said channel to permit the occlusion orifice of said sphincter body to surround the patient's lumen.

24. The elastomechanical sphincter according to claim 23, also including closure means by which to releaseably connect said sphincter body together at said channel, said closure means having a pair of legs being received in respective apertures formed in said body at opposite sides of said channel.

25. The elastomechanical sphincter according to claim 24, further including an enlarged portion formed at the end of each of the legs of said closure means, said enlarged portions projecting outwardly of said sphincter body when said legs are received in said respective apertures such that the force needed to withdraw said closure means from said sphincter body is greater than the force needed to insert said closure means into said body.

* * * * *